(12) United States Patent
Buff et al.

(10) Patent No.: US 11,389,224 B2
(45) Date of Patent: Jul. 19, 2022

(54) PNEUMATIC STRIKING TOOL FOR TREATMENT OF BONES IN HIP OPERATIONS AND METHODS FOR APPLYING THE STRIKING TOOL

(71) Applicant: IBAG MEDTECH AG, Kloten (CH)

(72) Inventors: Dominic Buff, Kloten (CH); Fabian Kalberer, Ebmatingen ZH (CH); Milos Nasic, Zürich (CH); Daniel Waldvogel, Oberembrach (CH)

(73) Assignee: IBAG MEDTECH AG, Kloten (CH)

( * ) Notice: Subject to any disclaimer, the term of this patent is extended or adjusted under 35 U.S.C. 154(b) by 0 days.

(21) Appl. No.: 16/337,597

(22) PCT Filed: Sep. 29, 2017

(86) PCT No.: PCT/IB2017/056019
§ 371 (c)(1),
(2) Date: Mar. 28, 2019

(87) PCT Pub. No.: WO2018/065873
PCT Pub. Date: Apr. 12, 2018

(65) Prior Publication Data
US 2022/0000531 A1 Jan. 6, 2022

(30) Foreign Application Priority Data
Oct. 3, 2016 (CH) .................................... 01305/16

(51) Int. Cl.
*A61B 17/92* (2006.01)
*A61B 17/00* (2006.01)
(52) U.S. Cl.
CPC ...... *A61B 17/92* (2013.01); *A61B 2017/0042* (2013.01); *A61B 2017/00544* (2013.01); *A61B 2017/924* (2013.01)

(58) Field of Classification Search
CPC A61B 2017/00535; A61B 2017/00544; A61B 17/1659; A61B 17/1662; A61B 17/1664; A61B 17/1668; A61B 17/88; A61B 17/8872; A61B 17/92; A61B 17/921; A61B 2017/922; A61B 2017/924; A61F 2/46; A61F 2/4603; A61F 2/4607
See application file for complete search history.

(56) References Cited

U.S. PATENT DOCUMENTS

| 5,102,051 A * | 4/1992 | Smith .................... B05B 7/0815 239/297 |
| 5,108,400 A * | 4/1992 | Appel ................ A61B 17/1659 173/91 |
| 6,758,842 B2 * | 7/2004 | Irion ........................ A61M 1/85 604/542 |
| 9,867,647 B2 * | 1/2018 | Mirza ................ A61B 17/0401 |
| 2011/0072947 A1 * | 3/2011 | Prout ..................... B21D 28/26 83/639.4 |

FOREIGN PATENT DOCUMENTS

DE 102013016171 A1 * 4/2015 ......... A61B 17/8872
DE 102013016171 * 11/2021

* cited by examiner

*Primary Examiner* — Larry E Waggle, Jr.
(74) *Attorney, Agent, or Firm* — Donald J. Ersler (57) ABSTRACT

The present invention relates to a pneumatic impact tool for hip surgery, comprising a housing with a cylinder/piston assembly with a pneumatically driven piston and a tool holder. The impact tool has two or more handles which are arranged at regular intervals around the cylinder/piston assembly.

11 Claims, 15 Drawing Sheets

PNEUMATIC STRIKING TOOL FOR TREATMENT OF BONES IN HIP OPERATIONS AND METHODS FOR APPLYING THE STRIKING TOOL

FIELD OF THE INVENTION

The present invention relates to a pneumatic impact tool for bone processing in hip surgery according to the preamble of claim 1 and to a method for using the impact tool according to the preamble of claim 13.

BACKGROUND OF THE INVENTION

Pneumatic impact tools have been used in hip surgery for many years. Compared to manual work, impact tools are advantageous in particular for the processing of a bone intended for receiving the artificial joint because the load on the bone can be minimized with a fine-tuned machine. Such impact tools are known from EP 0 452 543 and EP 0 617 926.

For some years now, the AMIS method (Anterior Minimally Invasive Surgery) has been offered as an alternative to the conventional hip replacement method. This surgical method is used more and more frequently, in particular due to the shorter rehabilitation time after the operation. In the AMIS method, the patient lies on his back, so that the surgeon has to prepare the bone intended for receiving the artificial joint from above. Although the known pneumatic impact tools could also be used in this surgical method, they are unhandy and due to the length of the impact tool, the surgeon would have to stand on an elevated platform to operate the impact tool properly. Therefore, the bone preparation for hip surgery according to the AMIS method is usually performed by the surgeon by hand.

SUMMARY OF THE INVENTION

The object of the present invention is to improve the known pneumatic impact tools while retaining their advantages in order to render them more convenient to use and compatible with the AMIS method. A further object of the present invention is to improve the implementation of the AMIS method using the proposed impact tool.

This is achieved by a pneumatic impact tool for hip surgery with the features of claim 1 and by a method for using the impact tool according to claim 13. Further features and embodiments will become apparent from the dependent claims and the advantages thereof are explained in the following description.

BRIEF DESCRIPTION OF THE DRAWINGS

FIG. 1a Top view of the pneumatic impact tool
FIG. 1b Side view of the pneumatic impact tool
FIG. 1c Front view of the pneumatic impact tool
FIG. 2a-b Inclining the patient's leg for better access to the femur
FIG. 2c Working direction of the pneumatic impact tool at an angle to the femur
FIG. 2d Side view of the pneumatic impact tool with an angle α between the handle plane and the longitudinal axis ZK of the cylinder/piston assembly
FIG. 2e Use of the pneumatic impact tool with tilted handles
FIG. 3 Top view of the pneumatic impact tool with handles 3, their longitudinal axes G having an angle β in the handle plane.

Figure 1A:
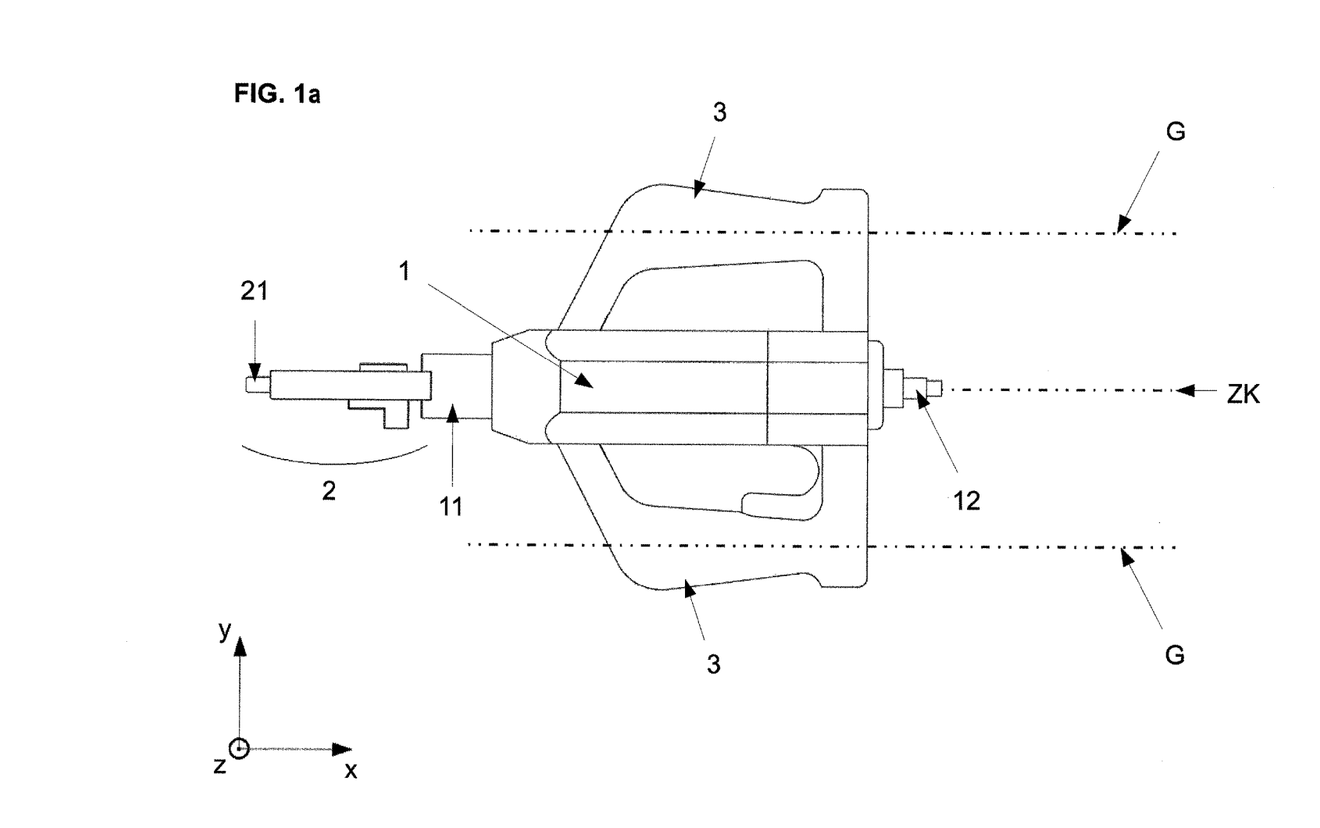
Figure 1B:
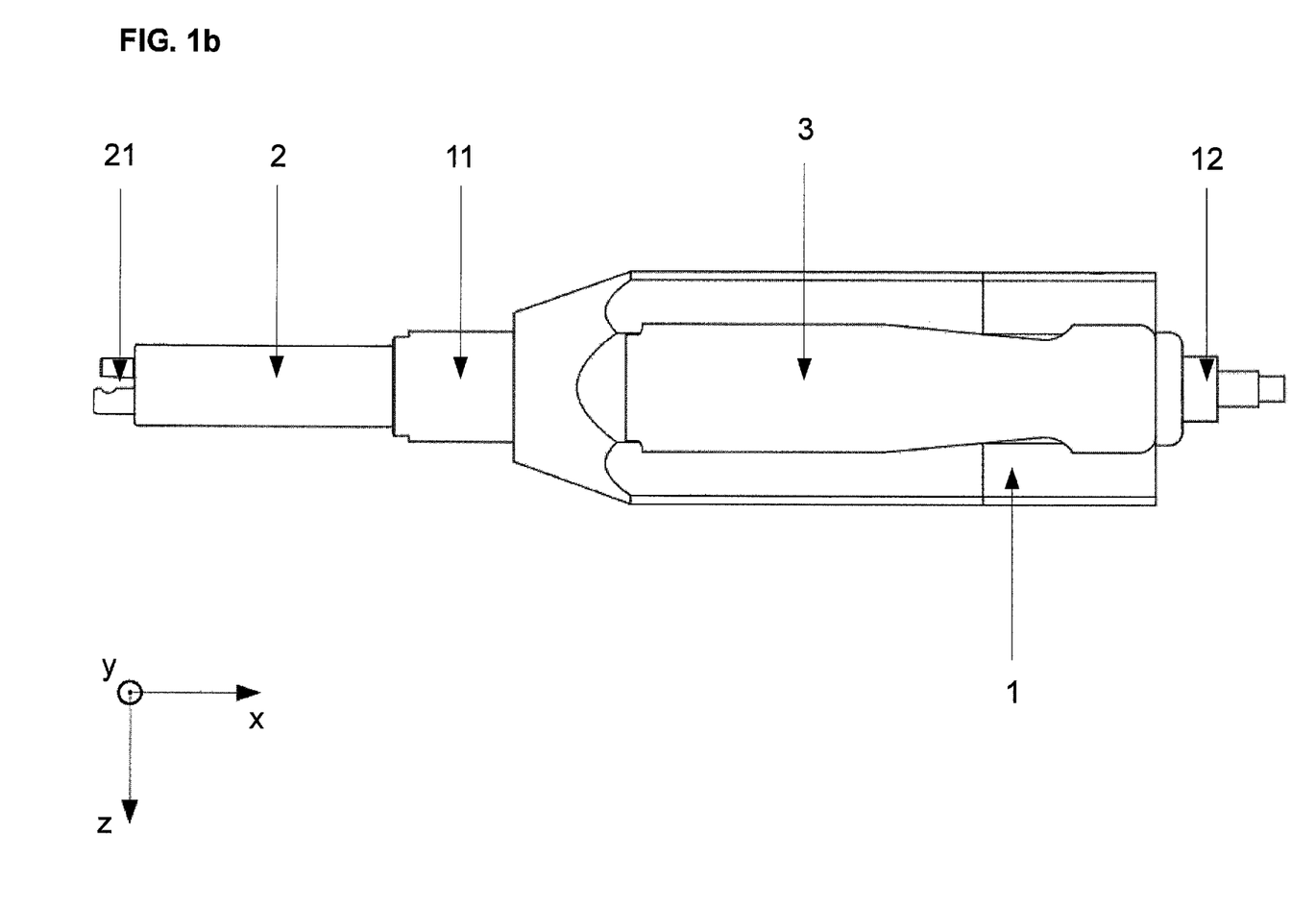
Figure 1C:
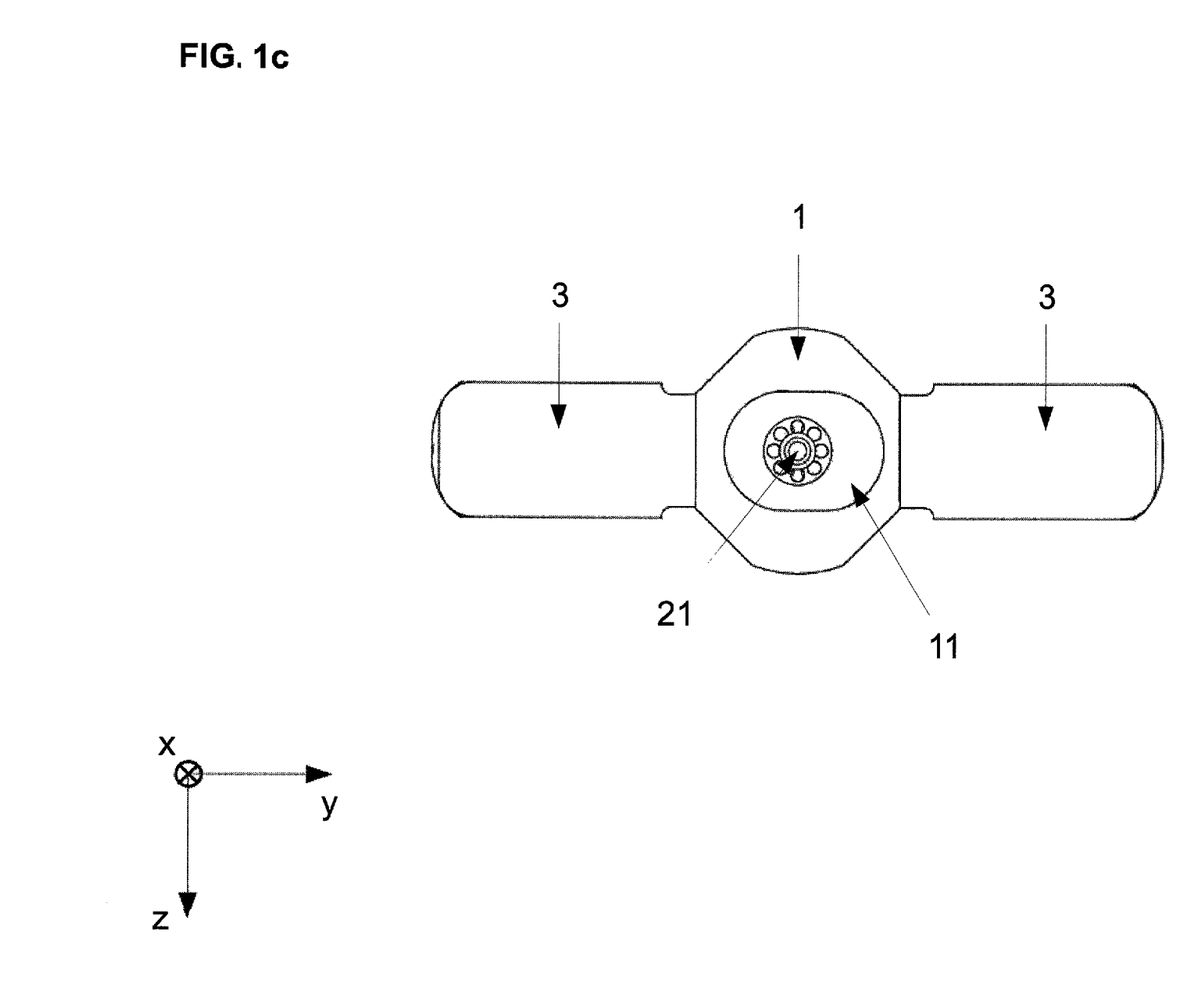

The present pneumatic impact tool consists of a housing 1, with which a tool holder 2 and two or more handles 3 are connected (FIG. 1a-c). Within the housing 1 is a cylinder/piston assembly, wherein a pneumatically driven piston moves back and forth in a cylinder. The tool holder 2 is connected to the cylinder/piston assembly via a connection 11 such that the forces and/or movements of the cylinder/piston assembly are transmitted to the tool holder 2 efficiently. In possible embodiments, the tool holder 2 can be driven for example in an oscillating, vibrating or pounding movement. The tool holder 2 has at the front end a connection 21 to which various tools for bone processing can be attached.

For the processing of the bones in order to receiving the artificial joint, the pneumatic impact tool must be operated with considerable force because of the hardness of the bone. In order to guide the impact tool in a clean and precise way and with as little effort as possible, stable and comfortable handles are advantageous. In the present invention it is intended that at least two handles 3 are connected to the impact tool. On the one hand, this provides a good stability and, on the other hand, it permits a precise guidance of the impact tool with little effort. The handles may be connected at both ends, as shown in FIG. 1, so as to reduce the risk that, when manipulating the impact tool, something will get caught by the handles or even simply comes between a handle 3 and the impact tool, such as e.g. a hose or a piece of cloth. This can be further improved by rounding off the handles resp. the connection between the handles 3 and the impact tool.

Several handles 3 on the impact tool allow holding the impact tool with both hands, which is even better for the stability and precision. In a preferred embodiment, two handles 3 are arranged on opposite sides of the cylinder/piston assembly. The two longitudinal axes G of the handles define the handle plane (FIG. 1a). Three, four or more handles 3 can also be arranged at regular intervals about the axis ZK. This has the advantage that during the processing of the bone, the surgeon can use different handles 3 around the impact tool, for example when he wants to change his working position without having to turn the impact tool.

Not only the number of handles 3 is essential for the good manageability of the pneumatic impact tool, but also their orientation relative to the housing 1. In the following, various advantageous orientations of the handles 3 are described, which substantially improve the ergonomics of the pneumatic impact tool.

In a possible embodiment of the invention, the longitudinal axis G of the handles 3 and the longitudinal axis ZK of the cylinder/piston assembly can e.g. be parallel (FIG. 1a). This embodiment is advantageous when the surgeon operates the pneumatic impact tool vertically in front of him, especially at chest level.

Figure 2A:
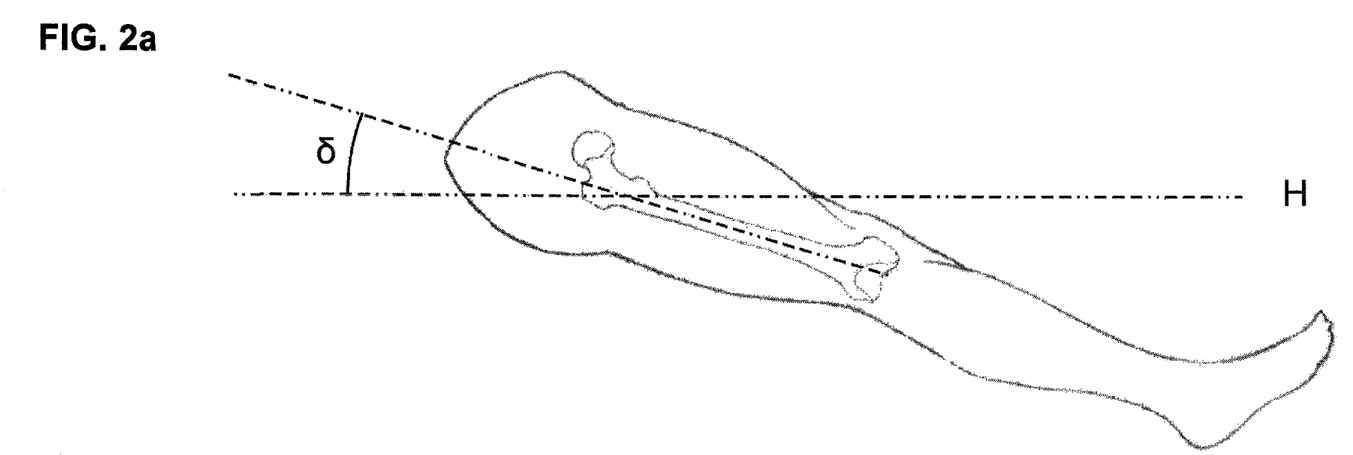
Figure 2B:
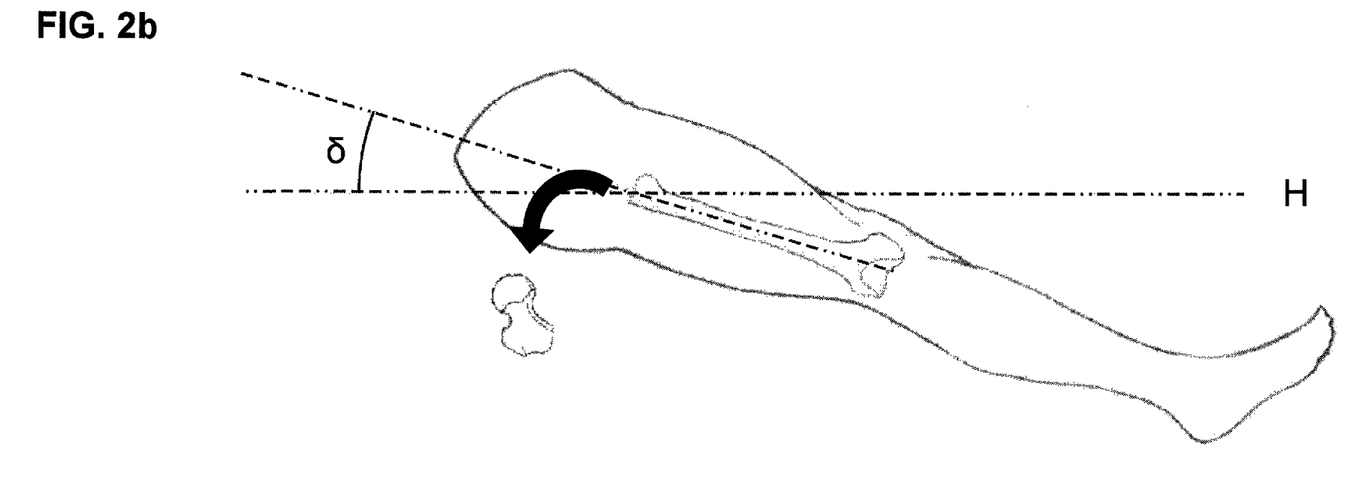
Figure 2C:
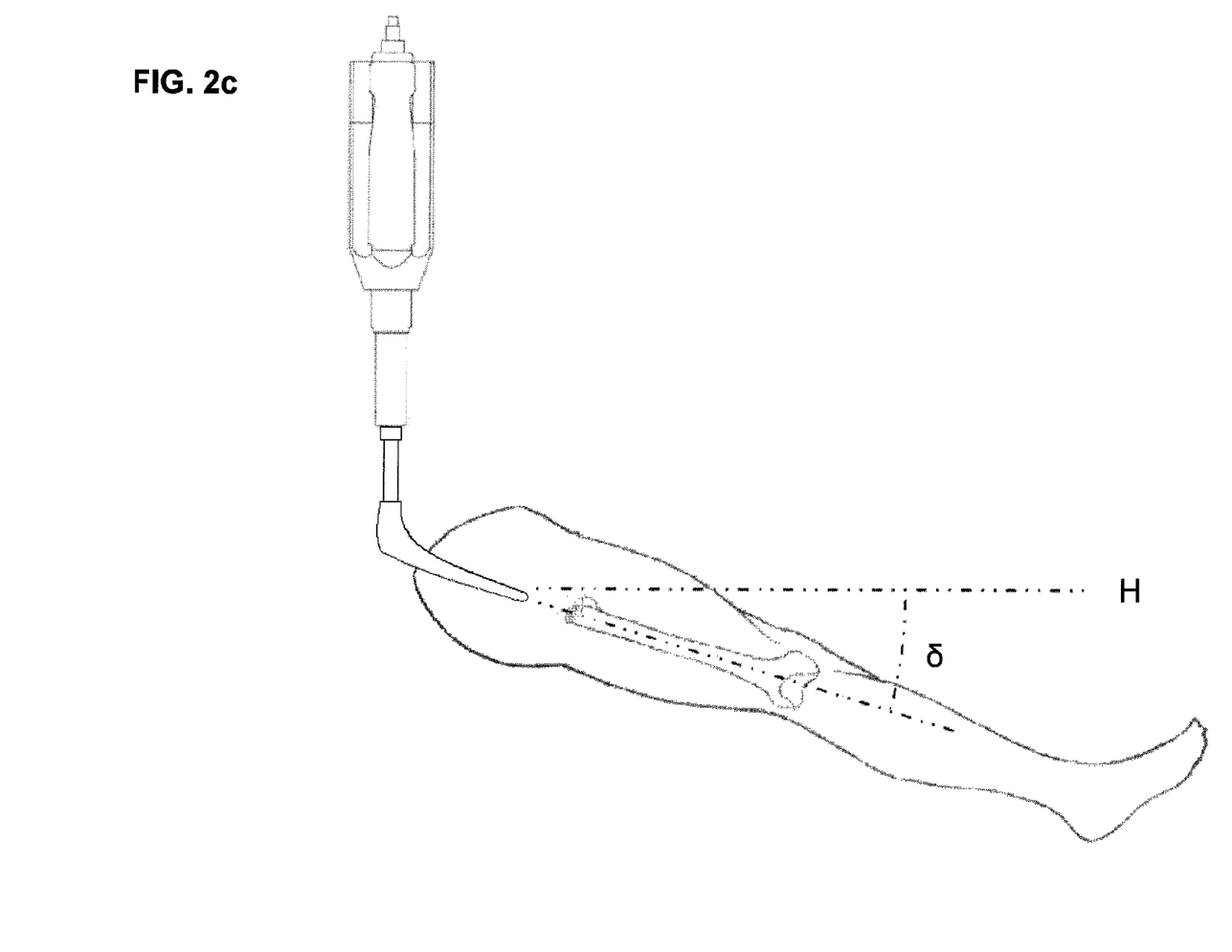
Figure 2D:
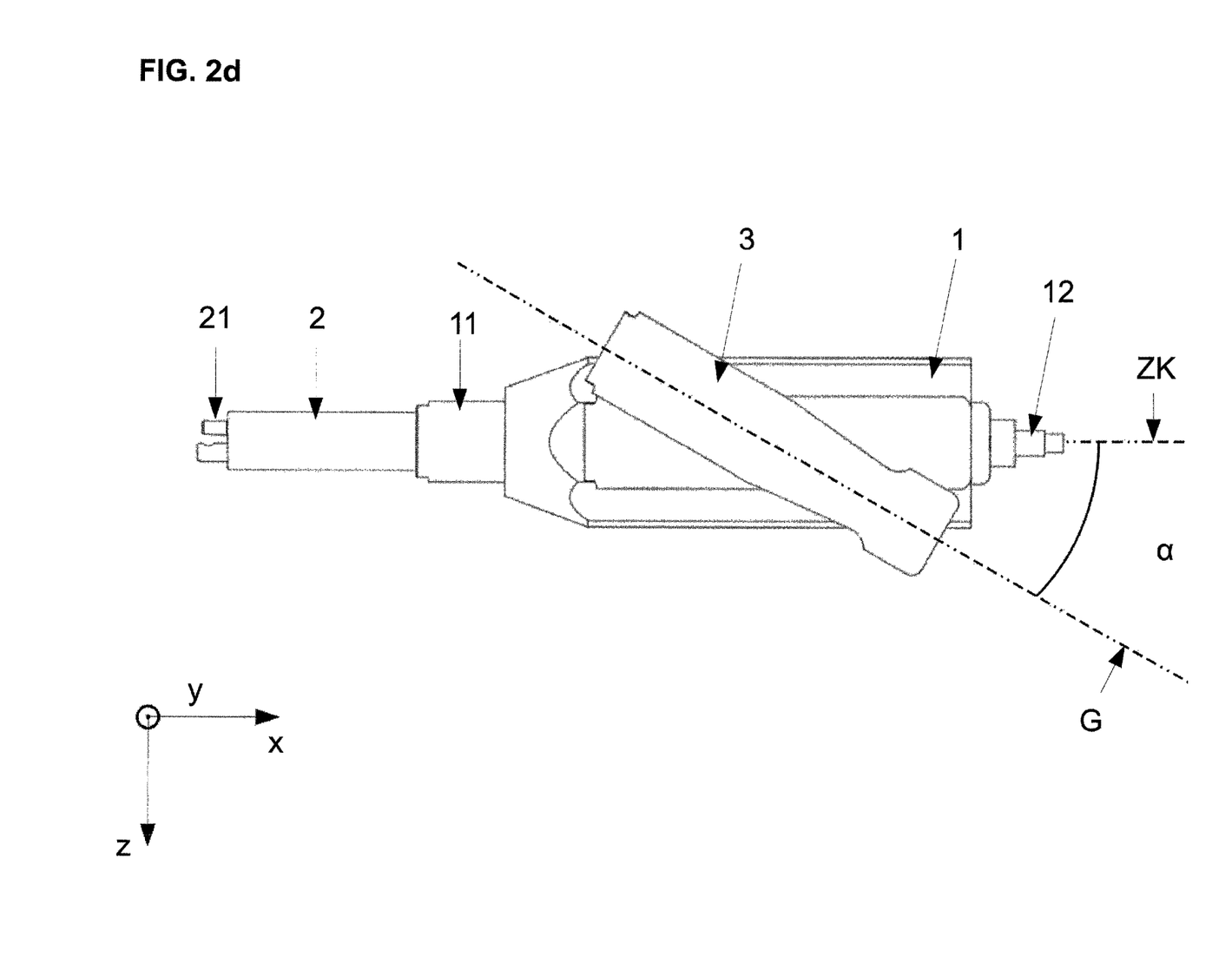
Figure 2E:
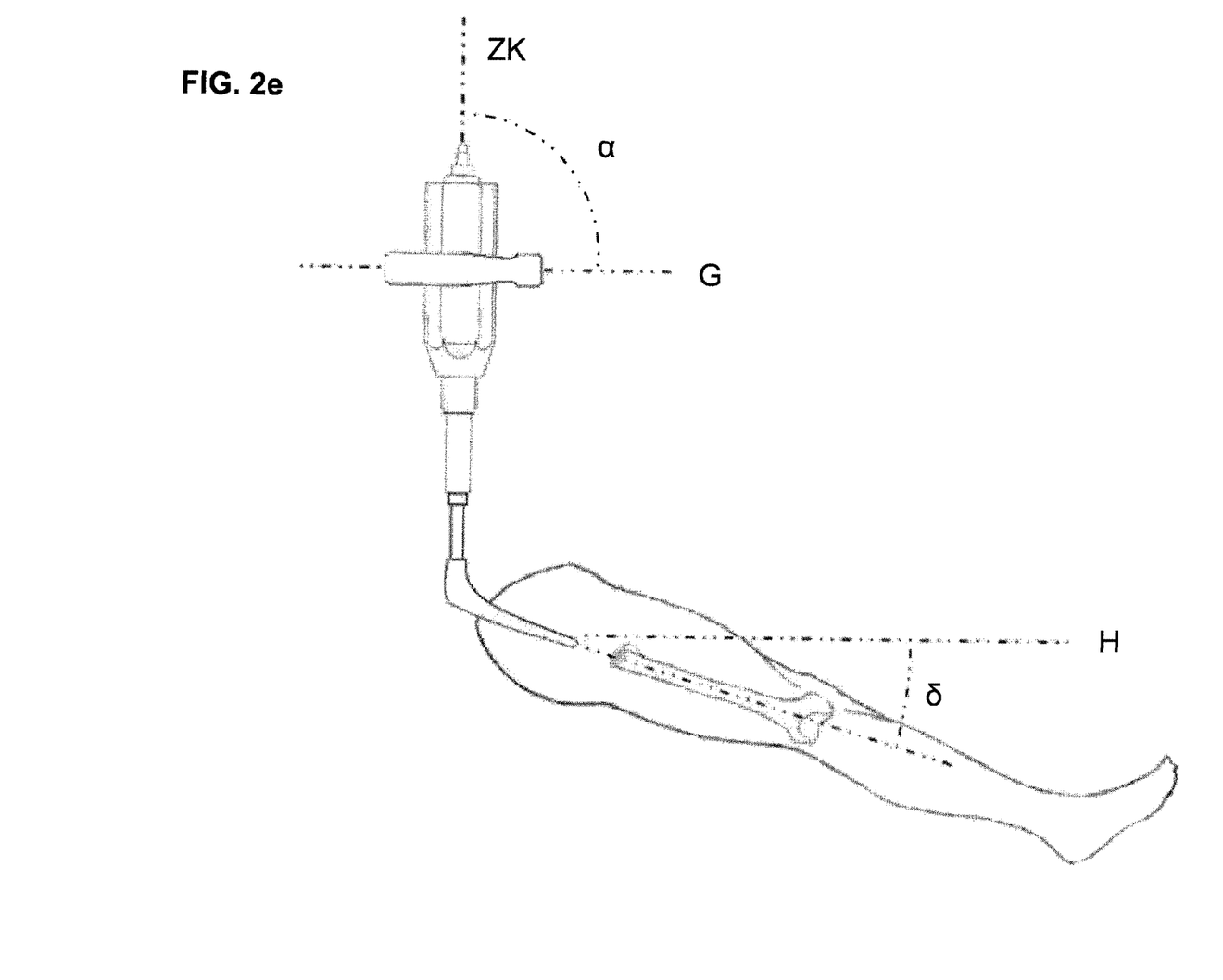

In a hip operation with the AMIS method, the patient lies on his back. For the operation, the patient's leg is turned outwards and inclined downwards at an angle δ of approximately 30° (FIGS. 2a-c). The bone for receiving the artificial joint is then worked on from above, whereby the impact tool cannot be operated in parallel behind the bone because the patient's body is in the way. In order to access the femoral head, the surgeon stands in front of the patient and next to his leg. For the processing of the bone, a bent, essentially banana-shaped tool is used. Accordingly, the impact tool is used more or less vertically for an optimal processing of the femur (FIG. 2c). In this working position, the surgeon holds the pneumatic impact tool vertically in front of him, approximately at chest level. In order to allow the surgeon to operate the impact tool optimally, it is conceivable that the handles 3 may be tilted by an angle α (FIG. 2d). This angle α is measured between the handle plane and the longitudinal axis ZK of the cylinder/piston assembly. Since the handles 3 are laterally displaced in the direction of the axis y with respect to the cylinder/piston assembly, the two axes G and ZK are not in the same plane and thus cannot intersect. Angles α between 0° to 90° are reasonable. In addition to the embodiment with a fixed angle α, the handles 3 could also be attached to the impact tool in such a way allowing them to rotate with respect to the cylinder/piston assembly in order to be able to adjust the angle either incrementally or continuously. This way, the impact tool can be used in a way giving the surgeon the best handle orientation for each application (FIG. 2e).

Figure 3:
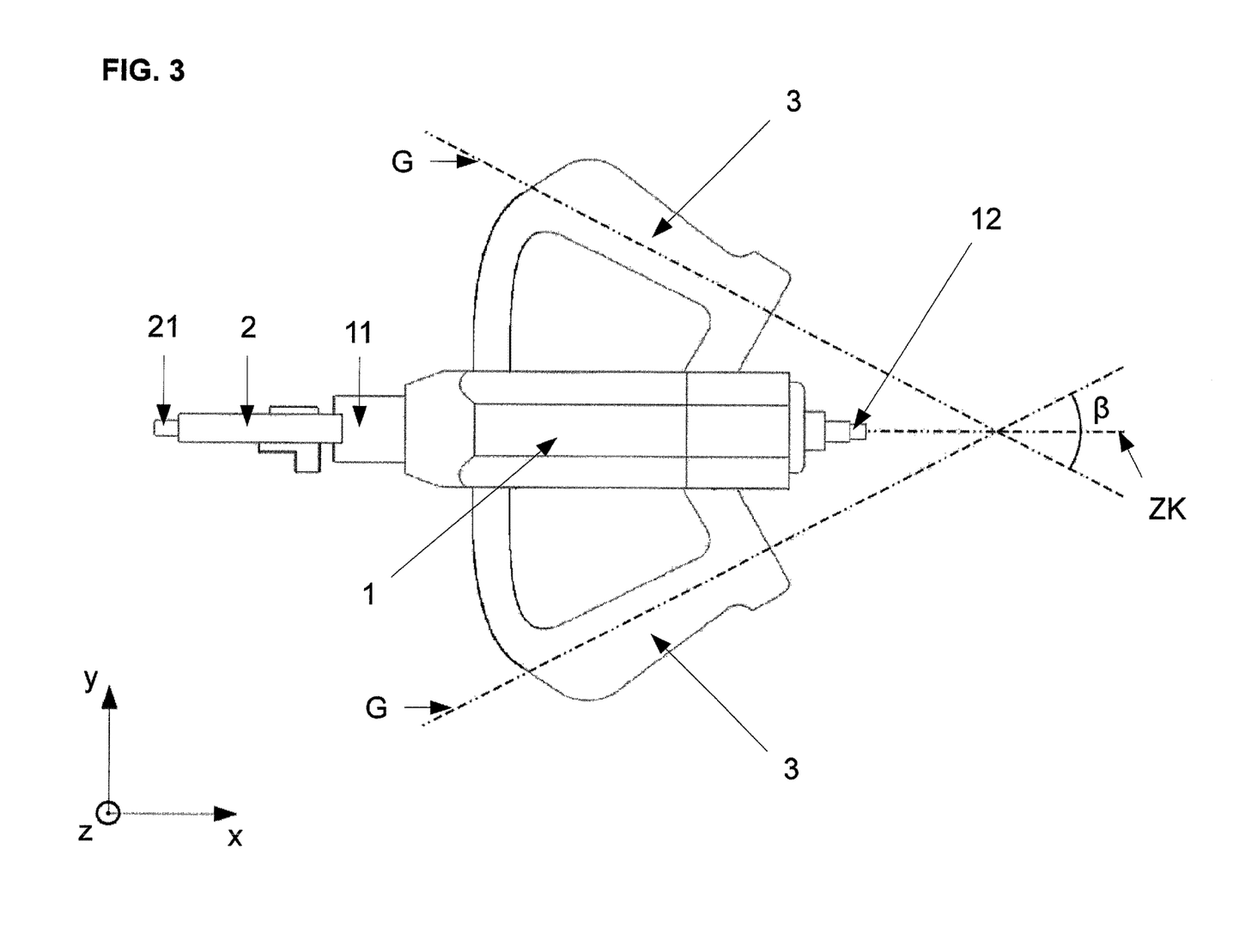
Figure 4:
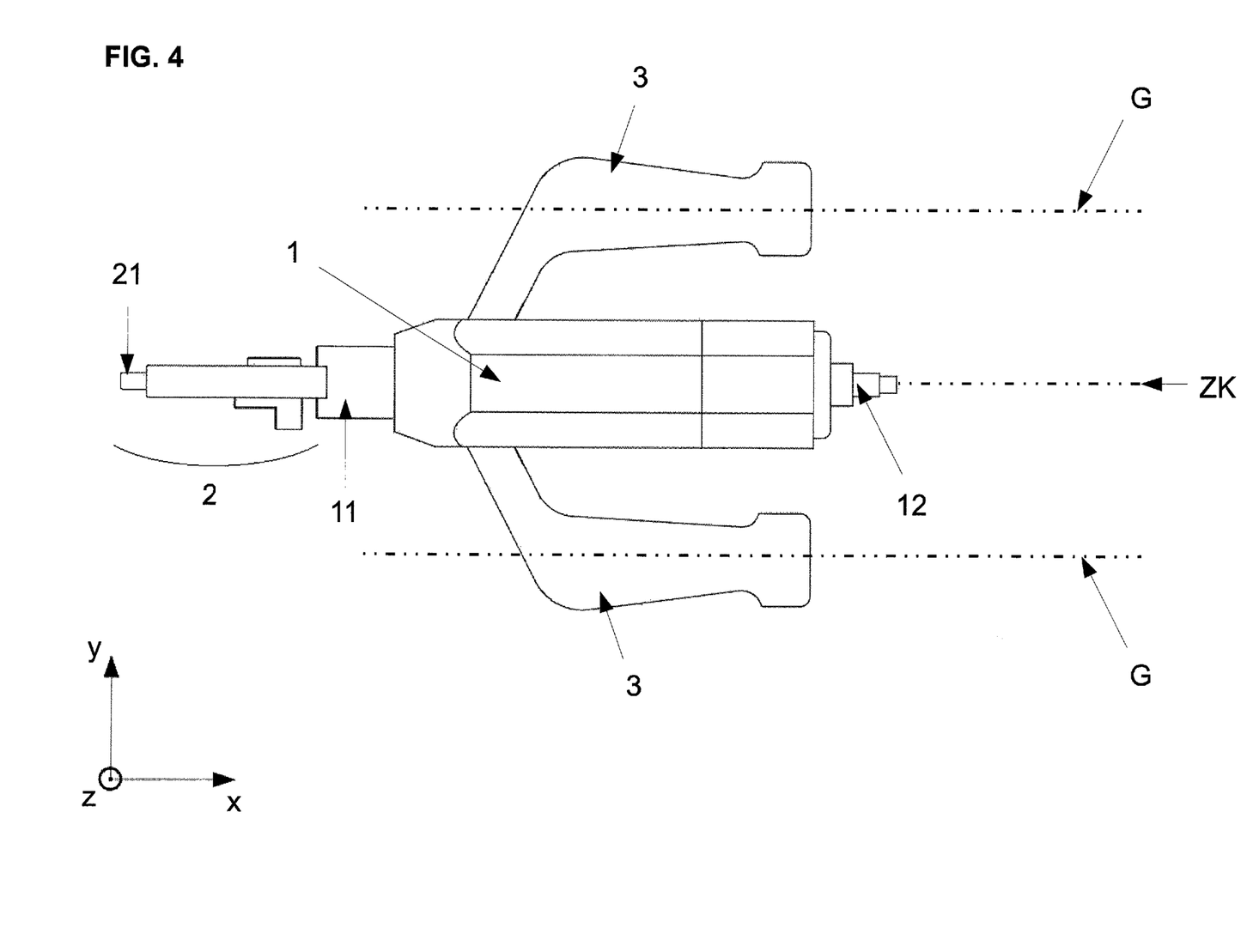
FIG. 4 Top view of the pneumatic impact tool with handles which are connected to the housing 1 at one end only
FIG. 5 Side view of the pneumatic impact tool with a bent tool holder
FIG. 6 Top view of the pneumatic impact tool with tool holder with offset
FIG. 7a Top view of the pneumatic impact tool with angled hose connection
FIG. 7b Side view of the pneumatic impact tool with angled hose connection
FIG. 7c Side view of the pneumatic impact tool with hose connection attached laterally
FIG. 8 Top view of the pneumatic impact tool with hose connection with rotatable ball joint The figures represent possible embodiments, which will be explained in the following description. The axes x, y and z define an orthogonal, right-handed coordinate system oriented according to FIG. 1.

In a further embodiment, the longitudinal axes G of the handles 3 can also have an angle β within the gripping plane (FIG. 3). This angle β advantageously contributes to the ergonomics of the pneumatic impact tool. If a user holds the impact tool e.g. vertically in front of him at chest level, his grip on the impact tool according to the embodiment of FIG. 3 may be more comfortable or more suitable for use than on the impact tool shown in FIG. 1a, where the longitudinal axes of the handles 3 are parallel. Similar to the position of the hands on the steering wheel of a car, i.e. not parallel on opposite sides of the steering wheel, the handle is more ergonomic. The longitudinal axes G of the handles 3 are thus not parallel, but form an angle β with the axis ZK. The optimal angle β can be different depending on the dimensions of the pneumatic impact tool. However, the angle β should not be too large, so that the axes G and ZK do not intersect inside the pneumatic impact tool, since otherwise losses in terms of guiding stability are to be expected.

Figure 5:
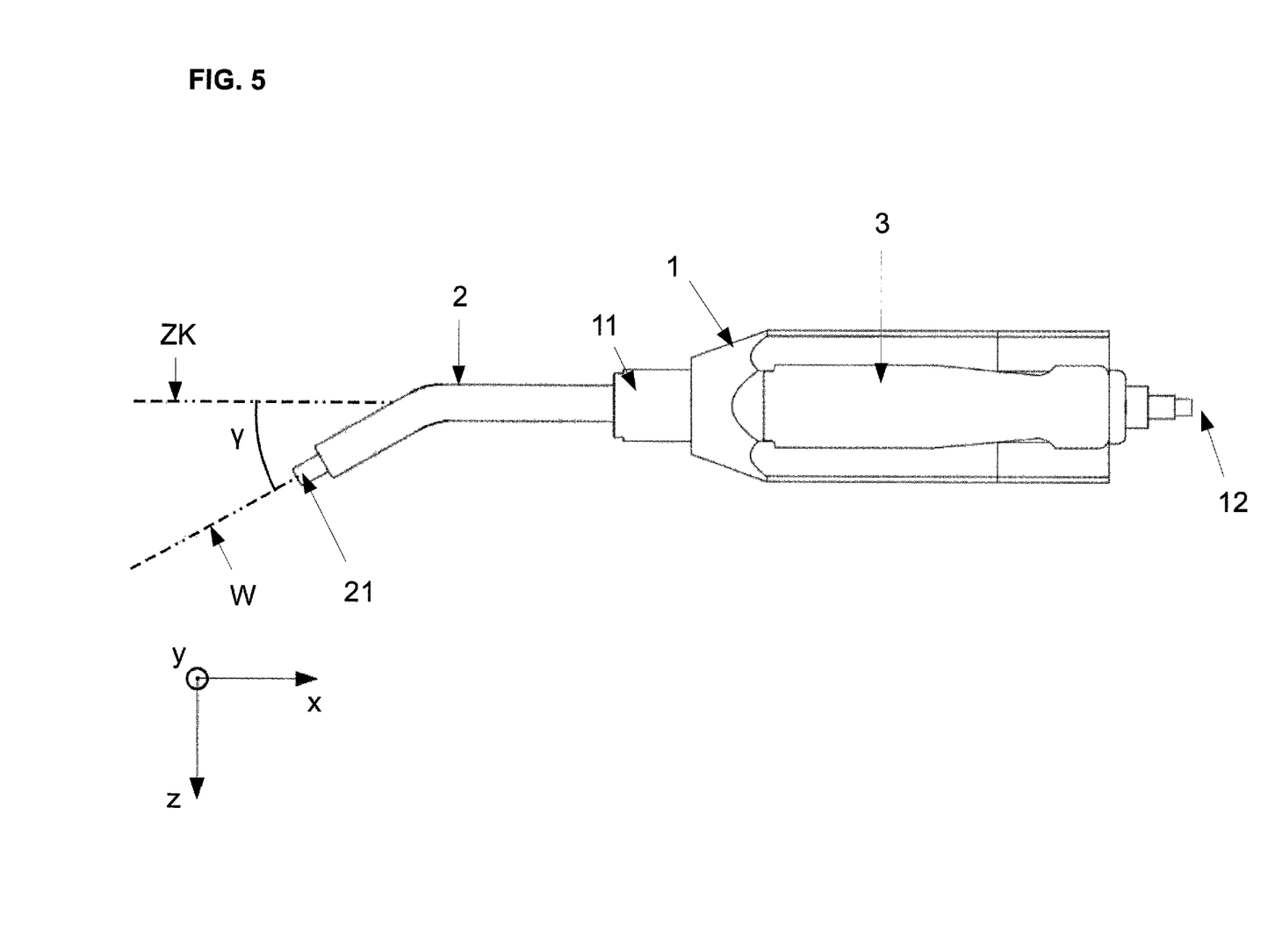

In addition to the shape and tilt of the handles 3 in various directions, the tool holder 2 can also be designed in different ways. In order to gain better access to the bone with the tool, the tool holder 2 may be provided with a bend (FIG. 5). The bend may have different angles γ between 0° and 90°, so that the surgeon does not have to operate the pneumatic impact tool with contorted arms and hands. This allows the surgeon to assume an ergonomic working position. In combination with the design options for the handles 3, the impact tool can be designed optimally and ergonomically for any operation.

Figure 6:
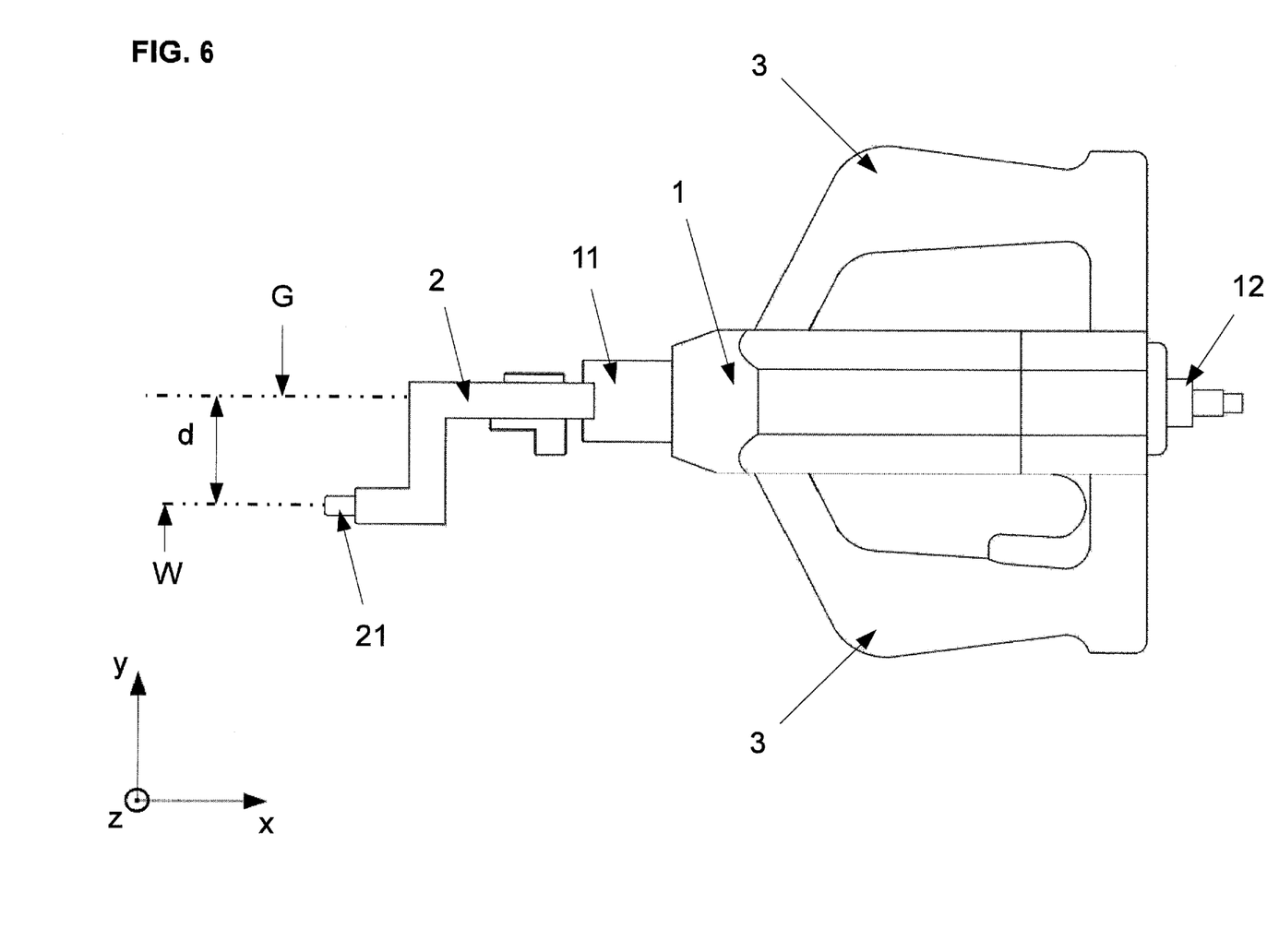

In an alternative embodiment, the tool holder 2 could also have an offset d, wherein the longitudinal axes W of the tool and ZK of the cylinder/piston assembly are offset by a distance d (FIG. 6). This distance d can also have the advantage that the surgeon needs to bend forward less, as the pneumatic impact tool can be held at a distance from the incision.

Figure 7A:
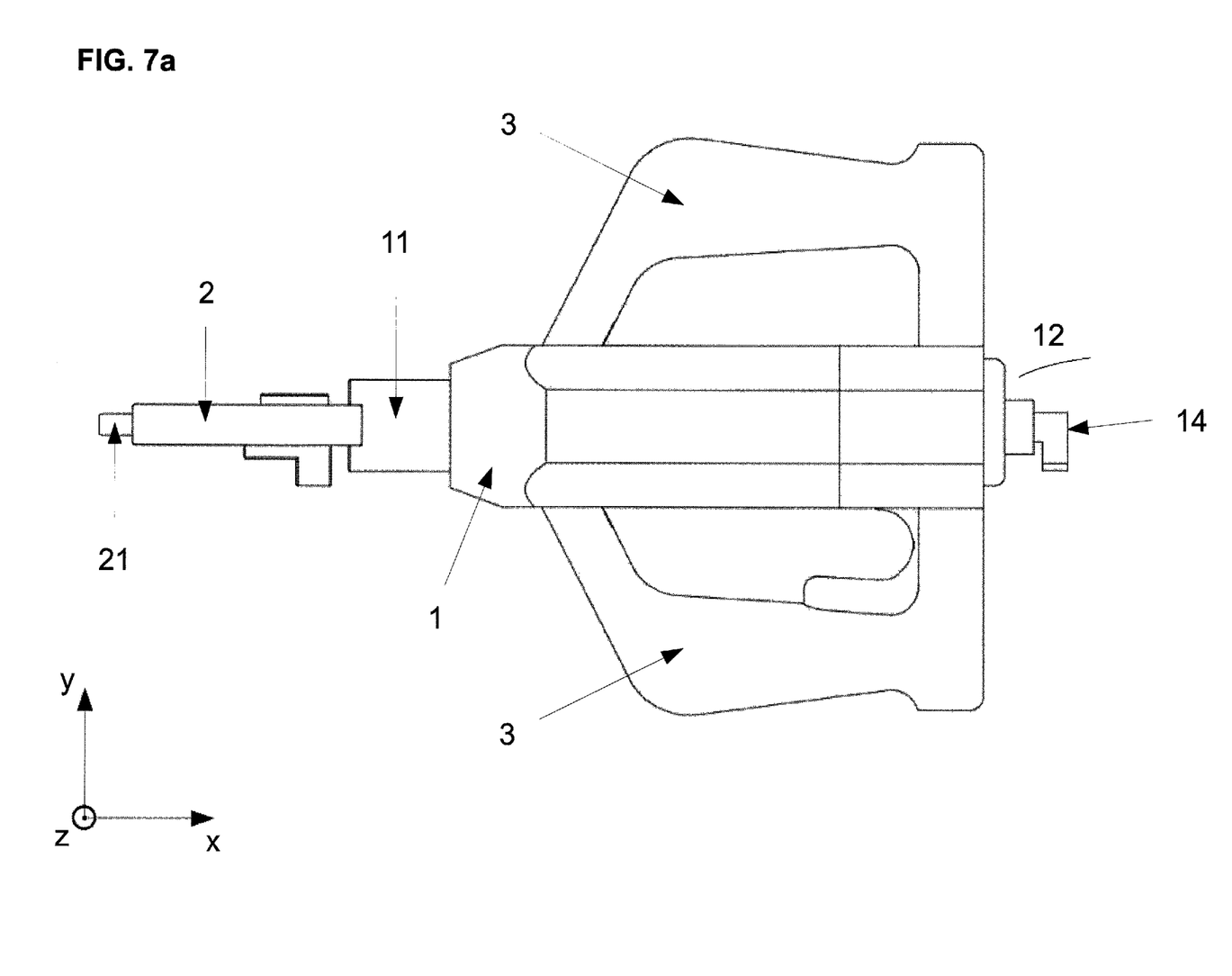
Figure 7B:
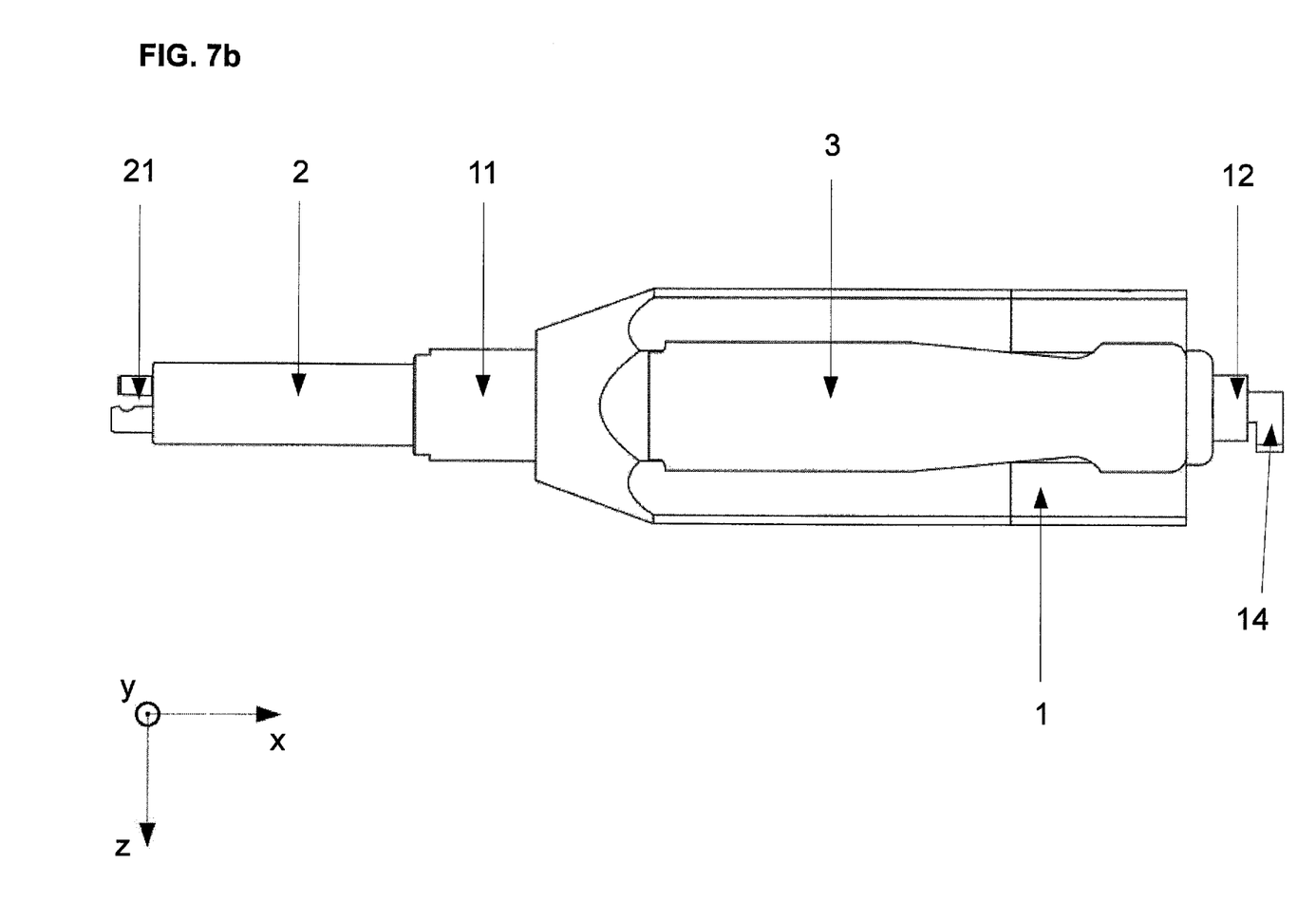
Figure 7C:
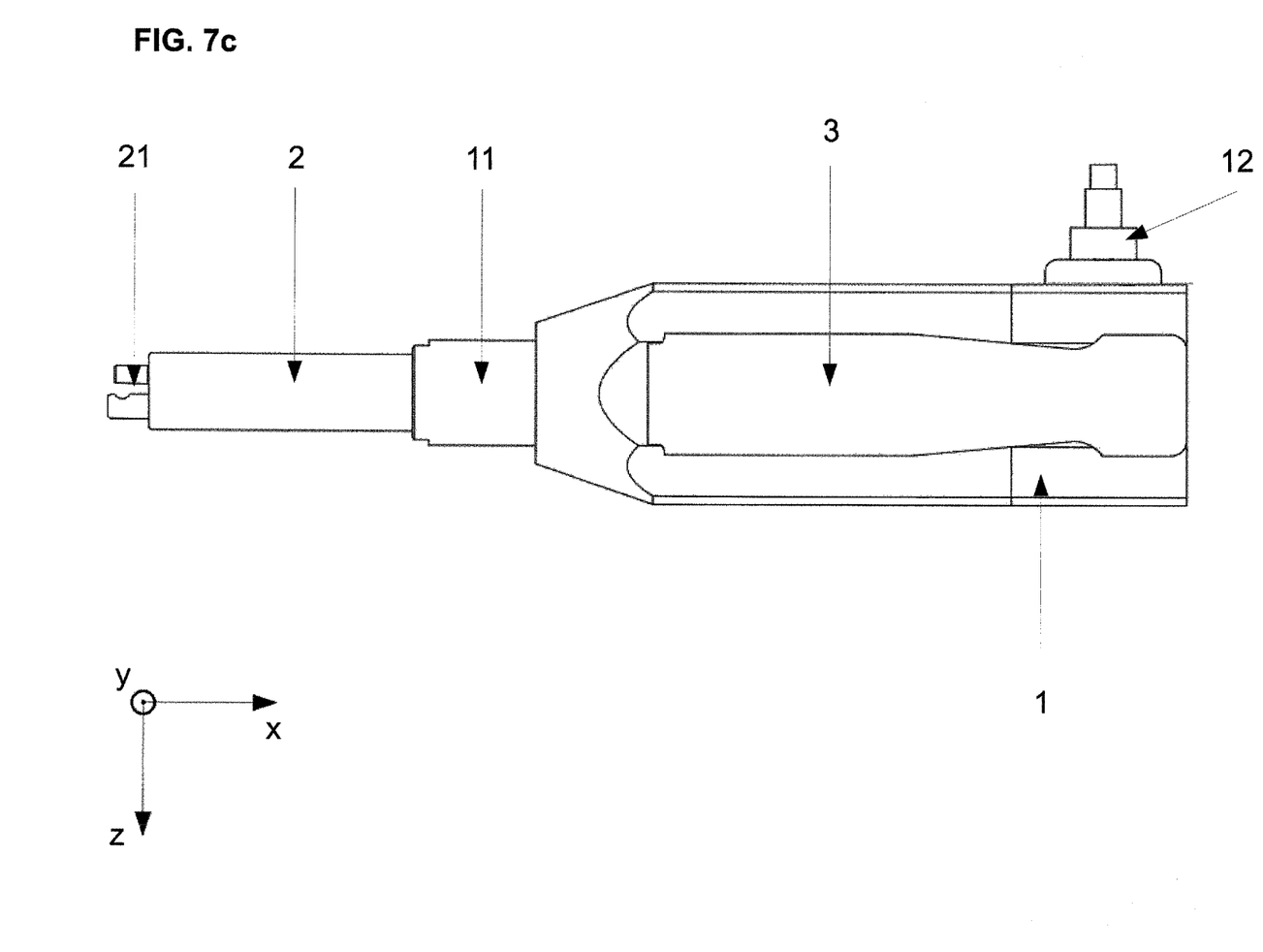
Figure 8:
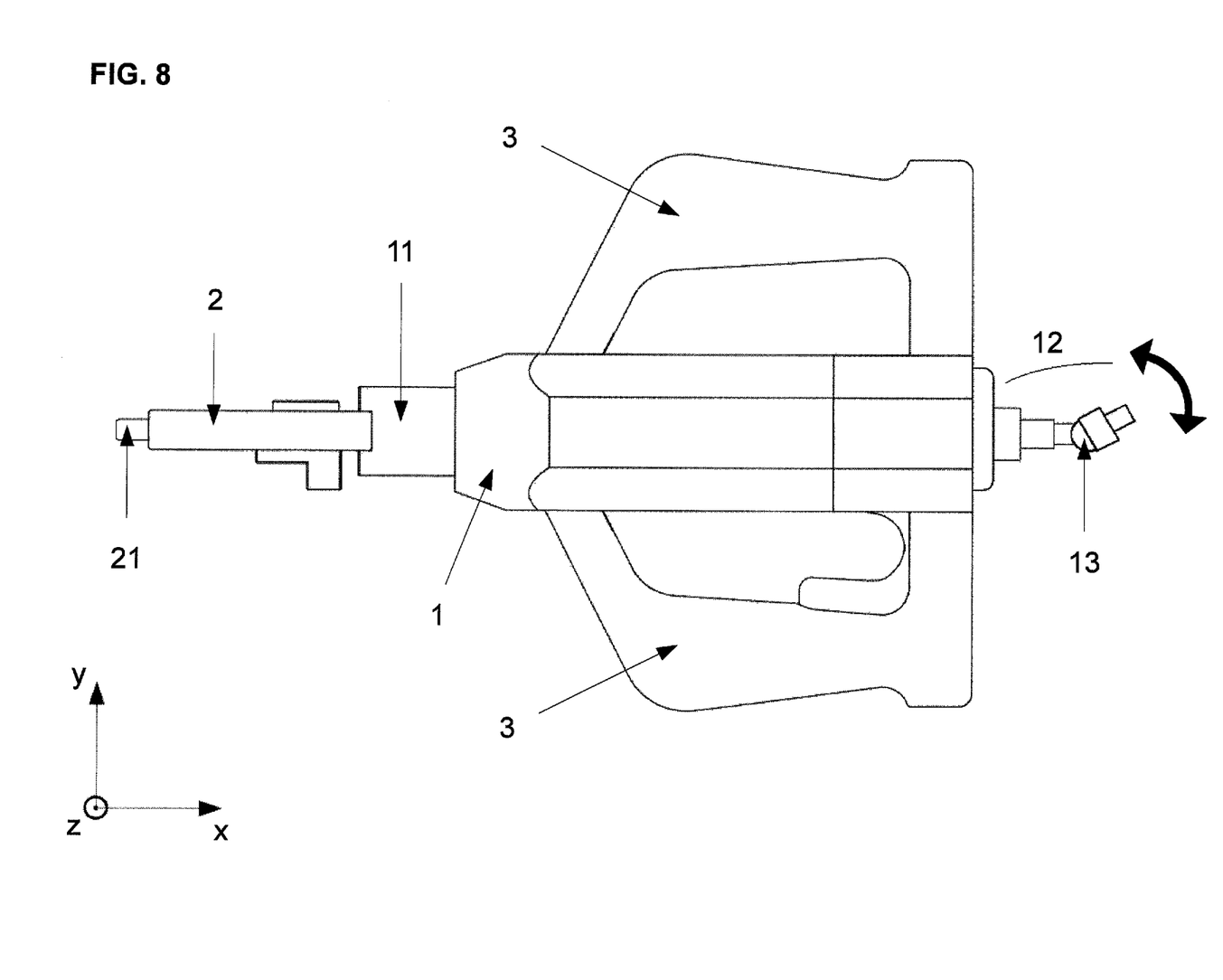

It is provided that the cylinder/piston assembly is driven with compressed air. Other drive variants are also possible, e.g. electricity. The compressed air can, in one embodiment, be supplied to the pneumatic impact tool via a hose. For better handling of the pneumatic impact tool, the hose connection 12 is ideally located at the rear end of the pneumatic impact tool. The connection can be straight and point backwards (FIG. 6) or form a 90° angle perpendicularly to the longitudinal axis ZK of the cylinder/piston assembly. If the connection is located in the prolongation of the longitudinal axis ZK of the cylinder/piston assembly, an angle connection 14 can be used (FIGS. 7a and 7b). Such an angle connection 14 can also be rotatable about the longitudinal axis ZK of the cylinder/piston assembly. Alternatively, the connection can also be mounted laterally on the housing (FIG. 7c). To withstand the required high air pressure, these hoses are often thick, stiff and heavy. In one embodiment, the hose connection 12 has a rotatable joint, for example a ball joint 13, so that the hose interferes as little as possible and exerts no tension on the impact tool (FIG. 8). In this embodiment with a rotatable ball joint, the pneumatic impact tool can be rotated in all directions independently from the hose without resistance.

The operation of the pneumatic impact tool is even more flexible when no hose is needed at all. This can e.g. be achieved by arranging a compressed air cartridge on the impact tool. In order to prevent the compressed air cartridge from making the impact tool larger and thus more cumbersome, it is intended that the handles 3 can be hollow and the compressed air cartridge can be inserted into this cavity. With several handles 3, multiple cartridges can be used, so that a larger driving force, a more constant drive and/or a longer autonomy is achieved.

The invention claimed is:

1. An impact tool for bone processing in hip surgery, comprising:
    a housing with a cylinder/piston assembly with a piston driven by compressed air or electricity, and a tool holder; and
    at least two handles are arranged at regular intervals around the cylinder/piston assembly, wherein longitudinal axes of the at least two handles and a longitudinal axis of the cylinder/piston assembly are substantially parallel.

2. The impact tool according to claim 1, wherein:
    a handle plane defined by the longitudinal axes of the at least two handles forms an angle α with a longitudinal axis of the cylinder/piston assembly.

3. The impact tool according to claim 1, wherein:
    the longitudinal axes of the handles are not parallel.

4. The impact tool according to claim 1, wherein:
    the tool holder has an angle γ relative to one of the at least two handles.

5. The impact tool according to claim 1, wherein:
    a connection for a pneumatic hose lies in a prolongation of a longitudinal axis of the cylinder/piston assembly.

6. The impact tool according to claim 1, wherein:
    a connection for a pneumatic hose is arranged perpendicularly to the longitudinal axis of the cylinder/piston assembly.

7. The impact tool according to claim 1, wherein:
a connection for a pneumatic hose has a rotatable joint and is rotatable around a longitudinal axis of the cylinder/piston assembly.

8. The impact tool according to claim 7, wherein:
the rotatable joint is a ball joint.

9. The impact tool according to claim 1, wherein:
at least one compressed air cartridge is connected to the pneumatic impact tool or integrated into the impact tool.

10. The impact tool according to claim 9, wherein:
the at least one compressed air cartridge is retained in ate least one of the at least two handles.

11. An impact tool for bone processing in hip surgery, comprising:
a housing with a cylinder/piston assembly with a piston driven by compressed air or electricity, and a tool holder; and
at least two handles are arranged at regular intervals around the cylinder/piston assembly, wherein an axis of the tool holder has an offset with respect to a longitudinal axis of the cylinder/piston assembly.

* * * * *